US011969303B2

(12) United States Patent
Faccioli et al.

(10) Patent No.: US 11,969,303 B2
(45) Date of Patent: Apr. 30, 2024

(54) SUPPORT STRUCTURE FOR A SURGICAL DEVICE AND RELATED METHOD FOR POSITIONING

(71) Applicant: Tecres S.p.A., Sommacampagna (IT)

(72) Inventors: Giovanni Faccioli, Monzambano (IT); Renzo Soffiatti, Nogara (IT)

(73) Assignee: TECRES S.P.A., Sommacampagna (IT)

( * ) Notice: Subject to any disclaimer, the term of this patent is extended or adjusted under 35 U.S.C. 154(b) by 934 days.

(21) Appl. No.: 16/961,003

(22) PCT Filed: Nov. 28, 2018

(86) PCT No.: PCT/IB2018/059402
§ 371 (c)(1),
(2) Date: Jul. 9, 2020

(87) PCT Pub. No.: WO2019/138277
PCT Pub. Date: Jul. 18, 2019

(65) Prior Publication Data
US 2020/0360107 A1    Nov. 19, 2020

(30) Foreign Application Priority Data
Jan. 10, 2018  (IT) .................. 102018000000689

(51) Int. Cl.
*A61B 90/50*   (2016.01)
*A61B 34/00*   (2016.01)
(Continued)

(52) U.S. Cl.
CPC ............. *A61B 90/50* (2016.02); *A61B 34/37* (2016.02); *A61B 34/70* (2016.02); *A61B 90/36* (2016.02);
(Continued)

(58) Field of Classification Search
CPC ......... A61B 90/50; A61B 34/37; A61B 34/70; A61B 90/36; A61B 90/39;
(Continued)

(56) References Cited

U.S. PATENT DOCUMENTS

| 5,893,543 A | * | 4/1999 | Emery | .................... A47K 1/09 |
| | | | | 248/205.5 |
| 6,099,490 A | * | 8/2000 | Turtzo | .................... A61F 5/028 |
| | | | | 2/311 |

(Continued)

FOREIGN PATENT DOCUMENTS

| WO | 2004/037065 A2 | 5/2004 |
| WO | 2008/001003 A2 | 1/2008 |

OTHER PUBLICATIONS

International Search Report for PCT/IB2018/059402 dated Feb. 12, 2019 (4 pages).

*Primary Examiner* — Myles A Throop
(74) *Attorney, Agent, or Firm* — Tutunjian & Bitetto, P.C.

(57) ABSTRACT

A support structure associable with a portion of the human body and usable for supporting a surgical device includes a frame delimiting at least one opening defining an area of surgery, wherein the frame has an upper support portion and a lower portion, means for connecting the frame to the predefined portion of the human body, wherein the connecting means include at least one support operatively connectable, in a removable manner, to the frame and to a predefined portion of the human body, without requiring any percutaneous intervention, and the at least one support is configured for allowing the removal of the frame from the predefined portion of the human body and for providing a reference for the exact repositioning of the frame along the predefined portion of the human body.

15 Claims, 4 Drawing Sheets

(51) Int. Cl.
*A61B 34/37* (2016.01)
*A61B 90/00* (2016.01)
*B25J 9/02* (2006.01)

(52) U.S. Cl.
CPC .............. *A61B 90/39* (2016.02); *B25J 9/023* (2013.01); *A61B 2090/374* (2016.02); *A61B 2090/3762* (2016.02); *A61B 2090/3966* (2016.02)

(58) Field of Classification Search
CPC ...... A61B 2090/374; A61B 2090/3762; A61B 2090/3966; A61B 34/10; A61B 90/14; A61B 90/18; A61B 50/20; A61B 90/57; A61B 34/30; A61B 2090/376; A61B 17/0218; A61B 2017/00486; B25J 9/023

See application file for complete search history.

(56) References Cited

U.S. PATENT DOCUMENTS

| | | | |
|---|---|---|---|
| 9,663,983 B2* | 5/2017 | Wexler | E06B 9/24 |
| 11,202,684 B2* | 12/2021 | Arnold | A61B 34/32 |
| 2003/0125753 A1* | 7/2003 | Saracione | A61B 90/14 |
| | | | 606/130 |
| 2004/0133078 A1* | 7/2004 | Edoga | A61B 17/02 |
| | | | 600/227 |
| 2005/0216026 A1* | 9/2005 | Culbert | A61B 17/17 |
| | | | 606/130 |
| 2006/0100501 A1* | 5/2006 | Berkelman | A61B 90/50 |
| | | | 600/415 |
| 2006/0212044 A1 | 9/2006 | Bova et al. | |
| 2008/0262527 A1* | 10/2008 | Eder | A61B 17/3403 |
| | | | 606/185 |
| 2009/0010726 A1* | 1/2009 | Brugman | B23Q 9/0042 |
| | | | 408/202 |
| 2012/0014759 A1* | 1/2012 | Sarh | B64F 5/10 |
| | | | 29/284 |
| 2014/0155796 A1* | 6/2014 | Yang | A61B 90/50 |
| | | | 602/19 |

* cited by examiner

SUPPORT STRUCTURE FOR A SURGICAL DEVICE AND RELATED METHOD FOR POSITIONING

TECHNICAL FIELD OF THE INVENTION

The present invention regards a structure associable with a predefined portion of the human body for supporting and positioning a surgical device usable during an operation on a patient.

STATE OF THE ART

The execution of a surgery operation which provides for the use of one or more surgical tools to be introduced in the human body, in accordance with a percutaneous procedure, is carried out by specialized surgeons. Such operations, in fact, even if they require an initial study and planning of the single movement steps of the surgical instrument and of the operations to be completed, are in any case subjected to a correlated risk.

In particular, the correct positioning and the subsequent movement of a surgical tool within the human body represent several of the most critical passages of the surgical procedure.

As stated above, for the purpose of reducing the risks to which the patient is subjected, it is known to study the predefined portion of the human body on which the surgeon must operate.

On such matter, images of such portion of the body of a patient are acquired, based on which the surgeon defines the inlet point of the instrument, the objective point to be reached within the body and the optimal path along which the surgical instrument is to be moved without causing damage to the internal structures of the human body.

The data thus acquired and processed, with particular reference to the planned path for the movement of the surgical instrument, is then used during the operation as a reference, to be examined for the actual positioning of the instrument within the human body.

During the surgery operation, in order to verify the actual positioning of the surgical instrument, it is known to use the same procedures for acquiring images used during the preliminary operation study and planning step, e.g. computerized tomography, magnetic resonance or radiological exams.

One limit of such procedure regards the difficulty encountered by the surgeon in manually and correctly maneuvering the instrument so as to accurately follow the previously-planned path, preventing the instrument from damaging structures within the human body.

There is therefore the need in the field to arrange a system that allows the surgeon to execute an operation in a manner such to be able to accurately reproduce the previously-planned steps, for the purpose of reducing to a minimum the risks connected to the operation itself.

One such aid system for a surgeon must be easy and practical to use, in the scope of a solution capable of causing the least possible discomfort for a patient who must be operated.

SUMMARY OF THE INVENTION

Hence, the main object of the present invention is to improve the state of the art relative to the means to be given to a surgeon for facilitating the insertion and the subsequent movement of a surgical tool relative to the body of a patient.

In the scope of such task, one object of the present invention is to provide a support structure associable with a predefined portion of the human body for supporting a surgical device bearing at least one surgical tool to be guided within the human body, which is practical and easy to use.

Another object of the present invention is that of providing a structure for supporting a surgical device whose mode of installation on a predefined portion of the body of a patient causes the least possible discomfort.

A further object of the present invention is that of providing a support structure of a surgical device whose positioning and connection relative to a predefined portion of the human body is simple to execute and requires a limited installation time.

According to one aspect of the present invention, a support structure is provided, associable with a portion of the human body, for supporting a surgical device according to the present application.

The present application refers to preferred and advantageous embodiments of the invention.

BRIEF DESCRIPTION OF THE DRAWINGS

Further characteristics and advantages of the present invention will be more evident from the detailed description of a preferred but not exclusive embodiment of a support structure for a surgical device usable on a predefined portion of the human body, illustrated as a non-limiting example in the enclosed drawing tables in which.

DETAILED DESCRIPTION OF THE INVENTION

With reference to the enclosed figures, a support structure for a surgical device according to the present invention is overall indicated with the reference number 1. More generally, the support structure 1 is configured so that, during use, it can be positioned and firmly associated with a predefined portion of the body of a patient for the purpose of providing a stable support for a surgical device bearing at least one surgical tool to be used during an operation.

In addition, the installation of the support structure 1 relative to the body of a patient is optimized in order to reduce to a minimum the discomfort of the patient himself.

For example, the support structure 1 can be used for supporting a surgical device such as a robotized system or robot for manipulating at least one surgical tool.

According to one version of the present invention, the support structure 1 can be used for the assisted positioning and movement of at least one surgical tool usable in the scope of a vertebroplasty procedure.

It is intended that the support structure 1 can likewise be used in further surgical procedures different from that indicated above, without any limitation.

The support structure 1 according to the present invention comprises at least one frame 2 associable with a predefined portion of the body of a patient.

The at least one frame 2 delimits at least one opening 3 which identifies an operation area on the body of a patient.

According to a preferred version of the present invention, the at least one frame 2 is configured like a picture frame. More precisely, the at least one frame 2 can be configured as a rectangular picture frame, which is extended longitudinally and aligned with the longitudinal extension of the spinal column C (see FIGS. 1 and 8).

The at least one opening 3, in such case, delimits an area substantially equal to the back of a patient.

According to such version, the at least one frame 2 can have two first sides 4, parallel to each other, and two second sides 5, parallel to each other. The two first sides 4 are alternated with and orthogonal to the two second sides 5.

The first sides 4 can have a length greater than that of the second sides 5.

It is intended that the at least one frame 2 can be shaped in a different manner, e.g. square or elongated, with a greater or lower number of sides with respect to the above-described version, still in the scope of a structure capable of delimiting at least one opening 3.

According to one version of the present invention, the at least one frame 2 can be rigid, in the sense that the relative position of the single sides that constitute it cannot be modified.

According to a further version of the present invention, not illustrated in the enclosed figures, the at least one frame 2 can comprise portions that are movable with respect to each other, in the sense that the relative position of the sides that constitute the at least one frame 2 can be modified.

The at least one frame 2 has an upper portion 6 and a lower portion 7.

According to one version of the present invention, the upper portion 6 can be configured for providing a support surface for a surgical device, as better described hereinbelow. In practice, according to such version the surgical device can be directly connected to the at least one frame 2 (see FIG. 1).

The lower portion 7, instead, is configured for being placed in abutment, during use, against the body of a patient or proximal thereto.

Figure 1:
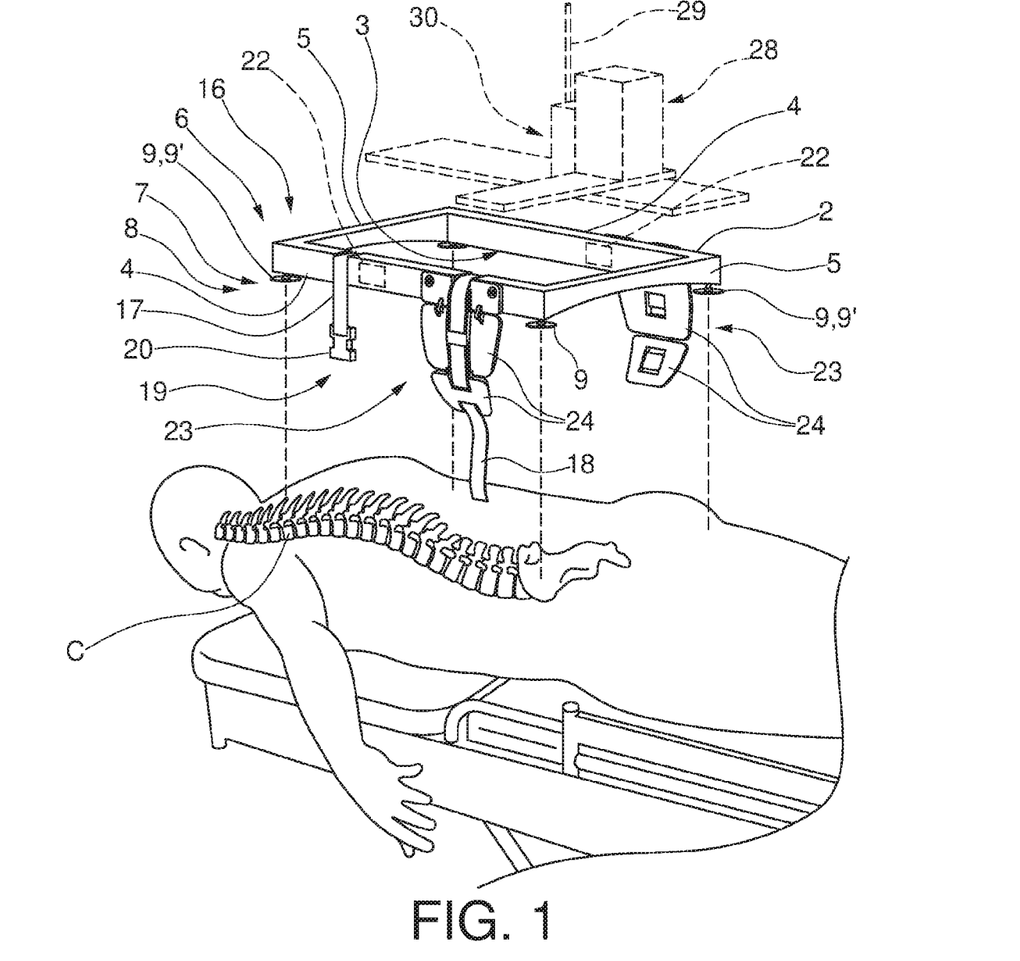
FIG. 1 is an exploded perspective view of a support structure for a surgical device according to the present invention.
Figure 6:
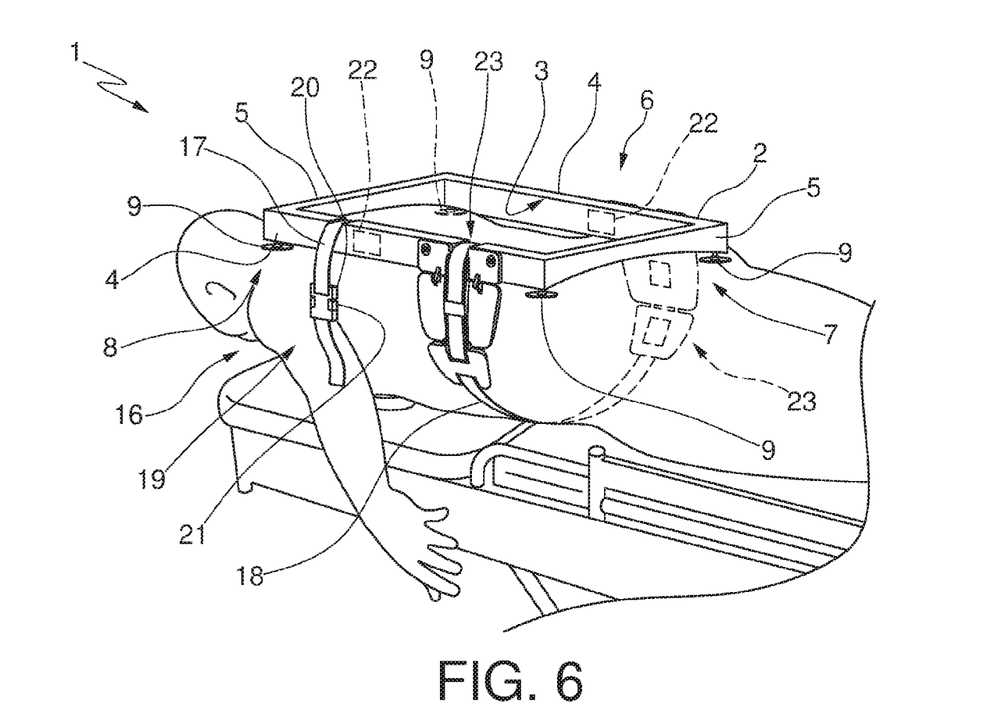
FIG. 6 is a perspective view of a support structure according to the present invention connected to a predefined portion of the body of a patient.

With reference to the embodiment illustrated in the enclosed FIGS. 1 and 6, it is observed that the at least one frame 2 is configured for abutting against the trunk of a patient.

According to such version, the installation of the support structure 1 occurs with the patient in supine position.

The at least one frame 2 can have at least one section of the lower portion 7 configured concave, at least at one of the two second sides 5, if present, with the concavity directed downward during use, in order to be better adapted to the morphological shape of the trunk of a patient and be more stable.

Figure 8:
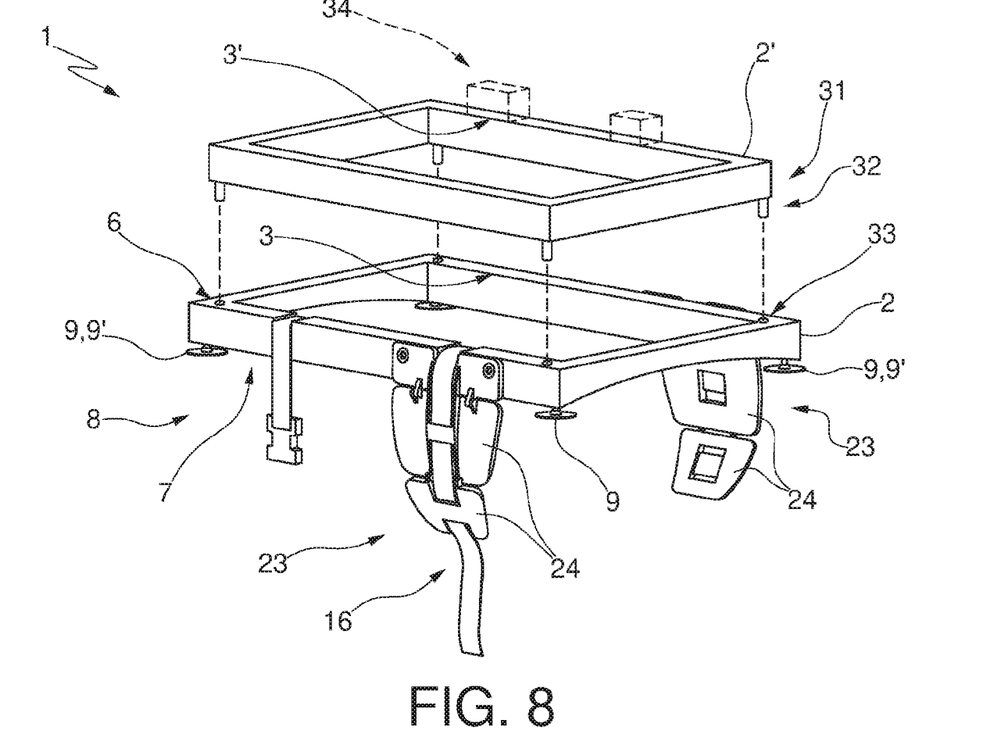
FIG. 8 is a detail view of several components of a further version of the support structure according to the present invention.

According to a further version of the present invention, illustrated as an example in the enclosed FIG. 8, the support structure 1 can comprise a further frame 2' associable above the at least one frame 2, for supporting a surgical device.

The further frame 2' is at least partially abuttingly supported by the at least one frame 2.

More in detail, the further frame 2' is provided for being associated with the at least one frame 2, in abutment against the upper portion 6 of the latter.

The further frame 2' delimits at least one through opening 3' which during use faces the at least one opening 3 delimited by the at least one frame 2, for the same purposes described in relation to the at least one opening 3 itself.

By way of example, the further frame 2' can have a configuration similar to that of the at least one frame 2, e.g. picture frame configuration.

The further frame 2' can comprise first connecting means, for connecting to the at least one frame 2, indicated overall with 31.

By way of example, the first connecting means 31 can comprise male elements 32. e.g. pins, which are extended below the further frame 2', adapted to engage respective female elements 33, e.g. seats, made in the upper portion 6 of the at least one frame 2.

It is intended that the position of the first connecting means 31 relative to the at least one frame 2 and to the further frame 2' can be reversed with respect to that described above.

According to a further version of the present invention, not illustrated in the enclosed figures, the first connecting means 31 can be configured in a different manner and comprise for example hook or jaw means adapted to selectively retain respective portions of the at least one frame 2.

As stated above, the further frame 2', if present, acts as support for the surgical device and for such purpose comprises second connecting means 34, not illustrated in detail in the enclosed figures, for the connection between the surgical device and the further frame 2'.

In fact, the use of a further frame 2' allows facilitating the positioning and the connection of at least one surgical device relative to the body of the patient.

For such purpose, indeed, the surgical device can be installed on the further frame 2' simultaneously with or before the installation of the at least one frame 2 on the body of a patient, without obstructing the positioning of the at least one frame 2, thus reducing the operating times and the discomfort of the patient himself.

The at least one frame 2 in fact is easier to move.

Hence, in order to associate the surgical device with the body of the patient, it is sufficient to mutually connect the further frame 2' and the at least one frame 2.

The use of a further frame 2' also allows easily adapting the support structure 1 substantially to any surgical device, since it is sufficient to use a specific further frame 2', adapted to the dimensions of a specific surgical device, without requiring the substitution of the entire support structure 1, hence in the scope of an extremely flexible use solution.

Further frames 2' with shapes different from each other can be configured for the engagement with a same at least one frame 2, facilitating a high flexibility of use of the support structure 1 according to the present invention.

According to one aspect of the present invention, the support structure 1 comprises means 8 for connecting the at least one frame 2 to a predefined portion of the human body.

In particular, the connecting means 8 are configured for attaining an initial positioning and connection of the at least one frame 2 relative to the predefined portion of the human body to be treated and, subsequently, for providing references for the exact repositioning of the at least one frame 2 in the same position of previous installation. More in detail, the connecting means 8 comprise supports 9 configured for abutting against and being connected to the human body and for supporting the at least one frame 2.

The connecting means 8 comprise at least one pair of supports 9.

The supports 9 are configured for supporting the at least one frame 2 in a raised position with respect to the predefined portion of the human body or in abutment against the same, according to the specific use requirements.

Each of the supports 9 is operatively connected to the at least one frame 2 and is configured for being able to be connected, in a temporary manner, to a predefined portion of the human body, without requiring any percutaneous intervention.

On such matter, it is observed that since no intervention of percutaneous type is necessary in such first step, the installation of the support structure 1 on the body of a patient can even be executed with the patient awake.

Each of the supports 9 has a lower connecting portion 10 that can be anchored, in a removable manner, to a predefined portion of the human body.

Figure 2:
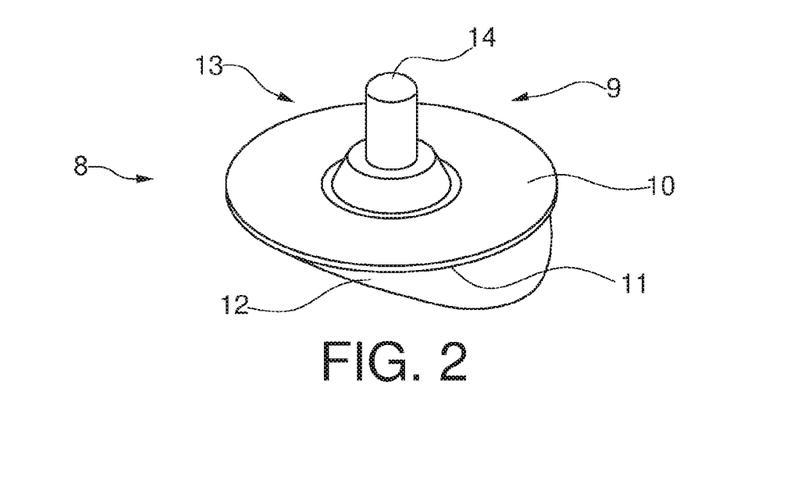
FIG. 2 is a top perspective view of a component of the support structure according to the present invention.

According to one version of the present invention, the lower connecting portion 10 can comprise an adhesive layer 11 in order to adhere to the skin (see FIG. 2).

According to such version, the support 9 can comprise a removable film 12 or a similar element, to cover and protect the adhesive layer 11. Indeed, the film 12 prevents dirt or contaminating agents from adhering to the adhesive layer 11, compromising the functionality thereof.

The film 12 can be removed before the connection of the support 9 to the body of a patient.

Figure 9:
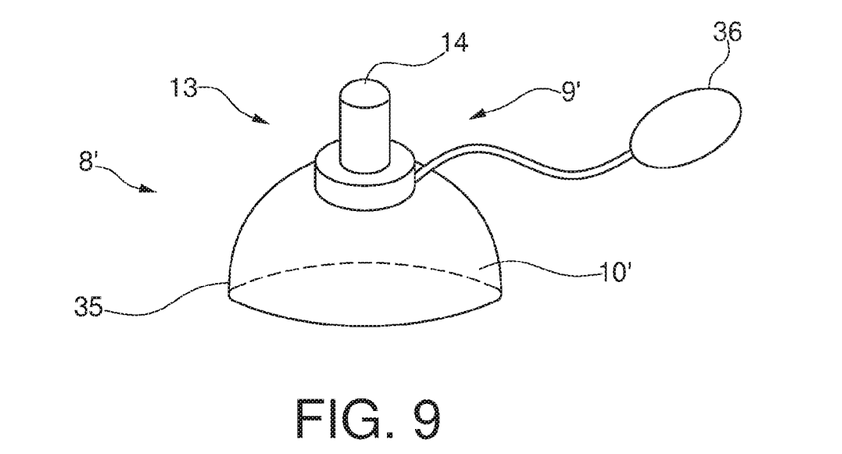
FIG. 9 is a detail view of a further version of a component of a support structure according to the present invention.

According to a further version of the present invention, illustrated as a non-limiting example in the enclosed FIG. 9, the supports 9' can comprise a lower connecting portion 10' comprising suction means 35 or the like.

The suction means 35 can be operatively connected to vacuum means 36, e.g. a manual actuation pump, for generating reduced pressure at the suction means 35 and causing a firm connection of the lower connecting portion 10' to a portion of the body of the patient.

Each of the supports 9, 9' is configured for being connectable, in a removable manner, to the at least one frame 2.

On such matter, each of the supports 9, 9' comprises an upper connecting portion 13 associable, in a removable manner, in the at least one frame 2.

The upper connecting portion 13 has a pin element 14 engageable, in a removable manner, in the at least one frame 2.

Figure 4:
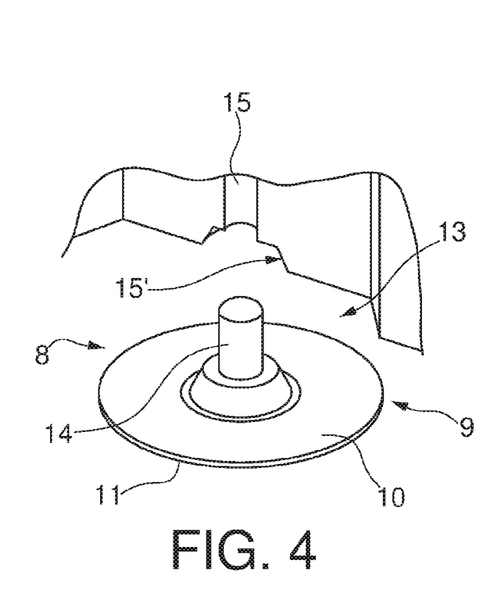
FIGS. 4 and 5 are detail views of several components of the support structure according to the present invention.
Figure 5:
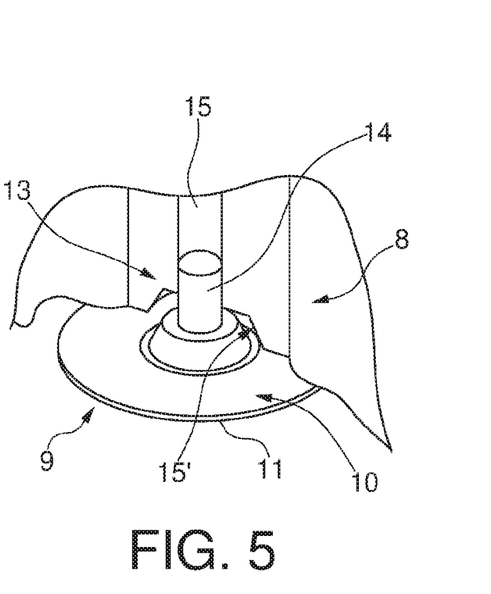

The at least one frame 2 has at least one seat 15, engageable by a respective pin element 14 (see FIGS. 4 and 5).

In particular, the coupling between the at least one seat 15 and a respective pin element 14 can be a shape or snap coupling.

The engagement between the pin element 14 and a respective at least one seat 15 is of removable type according to the aims that will be described hereinbelow.

The at least one seat 15 is made at the lower portion 7 of the at least one frame 2.

More in detail, the at least one seat 15 is extended through the lower portion 7 along a blind section or a section passing through the at least one frame 2, without any limitation.

The number and the arrangement of the at least one seat 15 along the at least one frame 2 can vary as a function of specific use requirements.

For example, it is possible to provide for a greater number of seats 15 than the overall number of supports 9, 9' to be used in a support structure 1, in order to be able to adjust the actual position of the supports 9, 9' themselves as a function of the morphology of the predefined portion of the body to which the support structure 1 is associated.

The at least one seat 15 can have a widened inlet portion 15' in order to facilitate the entrance of the at least one pin element 14 at its interior (see FIGS. 4 and 5).

With reference to the embodiment of the support structure 1 illustrated in the enclosed FIGS. 1, 6 and 8, the connecting means 8 comprise four supports 9, 9' each positioned in proximity to an edge of the at least one frame 2.

The number and the arrangement of the single supports 9, 9' can vary as a function of the shape of the at least one frame 2 and of specific use requirements and therefore can differ from that described above.

Moreover, it is intended that the supports 9 and 9' can be associated with at least one frame 2 in an interchangeable manner, since initially supports 9' can be used and then supports 9 can be used to substitute the first, for the purposes that will be better described hereinbelow.

The support structure 1 according to the present invention allows the installation of the at least one frame 2 in a pre-established portion of the human body along with the possibility of removing the at least one frame 2 and being able to subsequently reposition it in the same position, in the scope of a solution that is easy and practical to use.

In particular, it is observed that the support structure 1 allows rapidly repositioning the at least one frame 2 in the position of original installation, in fact reducing the discomfort for the patient.

The support structure 1 comprises band means 16 associated with the at least one frame 2 in order to connect the same to a pre-established portion of the human body and to firmly retain it in position.

The band means 16 can comprise adjustable belts, pull bands or similar band elements, whose number and arrangement can vary as a function of the configuration of the at least one frame 2 and specific use requirements.

With reference to the embodiment illustrated in the enclosed FIGS. 1 and 6, the band means 16 comprise at least one front band 17 and at least one rear band 18.

According to one version of the present invention, the band means 16 can comprise a pair of front bands 17, connected to opposite sides of the at least one frame 2, adapted to encircle/fasten around a predefined portion of the human body on opposite sides, firmly retaining it.

The support structure 1 can comprise coupling means 19 for mutually connecting the band means 16 to the at least one frame 2 or to each other.

The coupling means 19 can be configured for making a connection by means of Velcro or, more generally, comprise a male element selectively engageable with a respective female element by means of snap connection or shape coupling.

By way of example, the support structure 1 illustrated in the enclosed FIG. 1 comprises coupling means 19 associated with the front belts 17 and comprising a male element 20, connected to one end of a first front belt 17, and a female element 21, connected to one end of a second front belt 17, in which the male element 20 is configured for selectively engaging the female element 21.

According to a further version of the present invention, not illustrated in the enclosed figures, the coupling means 19 can comprise a clamp closure element for the purpose of adjusting the tension with which the band means 16 can be tightened around the predefined portion of the human body.

According to one version of the present invention, not illustrated in the enclosed figures, the support structure 1 can comprise means for adjusting the tension with which the band means 16 are associated with predefined portions of the body of a patient.

The band means 16 collaborate with the connecting means 8 in order to maintain the support structure 1 firmly in position relative to the pre-established portion of the body.

According to one version of the present invention, the at least one frame 2 and if present the further frame 2' can be made of radiolucent material, so as to not interfere with possible radiological image acquisition procedures or computerized tomography or magnetic resonance procedures.

According to one version of the present invention, the at least one frame 2 can comprise at least one pair of markers 22 adapted to define references along predefined portions of the at least one frame 2.

The markers 22 are used for positioning the at least one frame 2 relative to the predefined portion of the body of a patient, as well as for verifying a subsequent repositioning thereof (see FIG. 6).

The markers 22 can be radiopaque in one version of the invention.

According to one optional version of the present invention, the support structure 1 can comprise a pair of lateral retention elements 23 associated with opposite sides of the at least one frame 2.

With reference to the embodiment illustrated in the enclosed FIGS. 1, 6 and 8, the support structure 1 comprises a first and a second lateral retention element 23, each placed at the opposite sides of the at least one frame 2.

Figure 7:
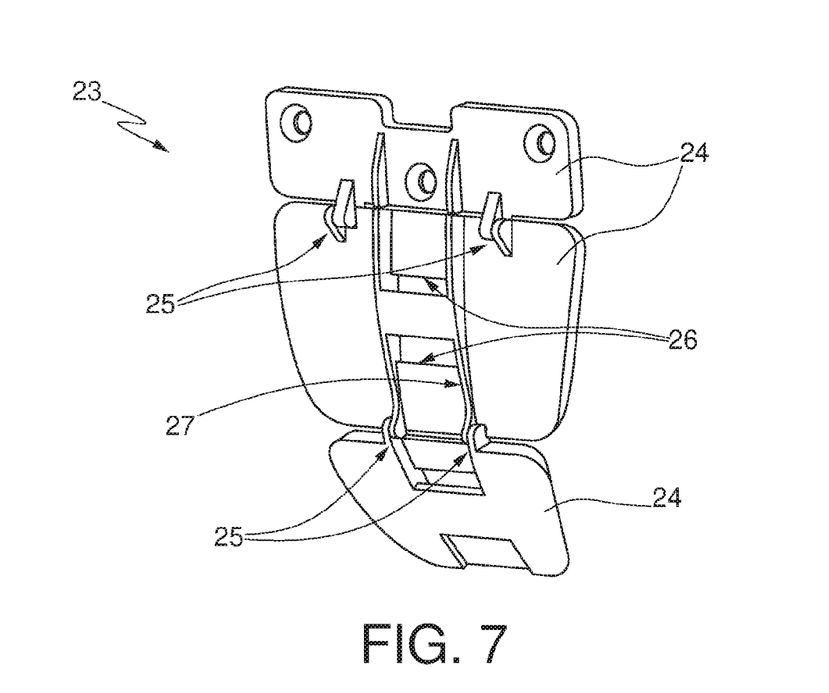
FIG. 7 is a detail view of a component of the support structure according to the present invention.

The lateral retention elements 23 are configured like small blades for firmly retaining the predefined portion of the human body between them, laterally enclosing it (see for example FIG. 7).

More in detail, each of the lateral retention elements 23 comprises plates or plate elements 24, articulated with each other and relative to the at least one frame 2, in a manner such that they can be brought close to or away from each other as a function of the dimensions of the portion of the human body to be retained between them.

By way of example, each of the lateral retention elements 23 can comprise two or more plates or plate elements 24.

By way of example, the single plates or plate elements 24 can be mutually connected by means of hinges 25 or rotary joints, in the scope of a solution that is easy and practical to use.

The lateral retention elements 23 can be selectively connected to the band means 16 in order to collaborate with the same and increase the stability of the connection of the support structure 1 to the body of a patient.

For such purpose, each of the lateral retention elements 23 can have at least one through opening 26 engageable by at least one of the band means 16.

The presence of at least one through opening 26 allows operatively connecting together the band means 16 and the lateral retention elements 23.

According to one version of the present invention, the lateral retention elements 23 can comprise at least one shaped seat 27, which is extended along at least one of the plates or plate elements 24, so as to retain the band means 16 along the retention elements 23. In practice, the at least one shaped seat 27 acts as a guide for maintaining the band means 16 extended and aligned along the retention elements 23 themselves.

As stated above, the support structure 1 has use in supporting a surgical device, for example configured for retaining and moving at least one instrument or surgical tool. On such matter, it is observed that also forming the object of the present invention is a system comprising a support structure 1 and a surgical device 28 for manipulating and moving a surgical instrument 29 relative to a predefined portion of the human body. The surgical device 28 is operatively connectable to the upper portion 6 of at least the frame 2 or to the further frame 2' if present.

With reference to that illustrated in the enclosed figures, the surgical device 28 and the surgical tool 29 are illustrated with dashed lines, for example in FIG. 1.

The surgical device 28 can comprise a Cartesian robot 30 adapted to retain at least one surgical tool 29 and to move the latter along a triad of orthogonal axes, possibly tilting it with respect to any one of said orthogonal axes (see FIG. 1).

According to one aspect of the present invention, the surgical device 28 can be operatively connected to a computerized processor, not illustrated in the enclosed figures, adapted to drive—in an automated or assisted manner—the at least one surgical tool 29 associable with the device 28.

The computerized processor can be configured for detecting the instantaneous position of the at least one surgical tool 29 relative to the portion of the human body on which the support structure 1 is installed, previously comparing it with a pre-established position in order to verify the correct movement of the at least one tool 29 along a pre-established path.

The movement of the at least one surgical tool 29 can therefore occur in a completely automated manner, under the supervision of at least one surgeon.

Alternatively, the movement of the at least one surgical tool 29 can be commanded by a surgeon in manual manner.

Hereinbelow, a description is reported of a method for the positioning and the possible repositioning of a support structure 1 in proximity to a predefined portion of the human body.

Initially, a support structure 1 is provided, comprising at least one frame 2, delimiting at least one opening 3 adapted to define an area of operation on a portion of the human body, and connecting means 8 engaged in respective seats 15 present in the at least one frame 2.

The connecting means 8 are then positioned at respective points indicated on the human body, achieved for example through the use of an indelible marking pen or a similar marker adapted for such purpose.

In order to define the points of connection of the support structure 1 to the human body, the supports 9' can be initially used for the purposes described hereinbelow.

In practice, the lower portion 7 of the at least one frame 2 is positioned in proximity to or in abutment against a predefined portion of the human body, by positioning the at least one opening 3 at the predefined portion of the human body, thus framing the operation area.

Then, during use, the means 8 for connecting to the body of the patient are associated. If the connecting means 8 comprise supports 9' provided with a lower connecting portion 10', the suction means 35 are positioned against the body of the patient and, by means of the vacuum means 36, they are constrained in position.

If the positioning of the connecting means 8 relative to the human body is not correct, the suction means 35 are released, thus disconnecting the connecting means 8 from the human body and one proceeds as indicated above up to obtaining the desired positioning.

At this point, with the connecting means 8 firmly connected to the human body, the at least one frame 2 is moved away from the connecting means 8, which are retained on the body of the patient, until the pin elements 14 are disengaged from the relative seats 15, actually disconnecting the at least one frame 2 from the body of the patient.

Then, with the marker, reference points are defined on the body of the patient in order to define the position at which the connecting means 8 must be positioned, in order to facilitate subsequent positioning of the same.

For example, with the marker, circles can be indicated on the body of the patient, such circles defined by the peripheral portion of the suction means 35 in abutment against the body itself.

Then, the suction means 35 can be removed.

The reference signs—e.g. circles—allow the subsequent positioning of the connecting means 8 in the previously-determined position.

The subsequent positioning of the connecting means 8 can occur within hours or possibly several days, so that the reference signs can remain on the body at least for one such time interval, thus ensuring correct positioning of the support structure 1. Then, the at least one frame 2 is provided with the connecting means 8 comprising a lower connecting portion 10 provided with an adhesive layer 11.

Before connecting such connecting means 8 with the body of the patient, it is necessary to remove the possible protection film 12 covering the adhesive layer 11. Then, the adhesive layer 11 is brought against the body of the patient, actually sticking the connecting means 8 on a predefined portion of the body.

The adhesive layer 11 must be centred relative to the references previously made on the body of the patient, in order to obtain the correct positioning of the support structure 1.

By means of possible markers 22 present in the at least one frame 2, the correct positioning of the at least one frame 2 itself relative to the human body can be further verified.

Then, the at least one frame 2 is firmly associated with the body of the patient by means of the band means 16, possibly adjusting the length thereof in order to ensure that the same firmly adhere against the body of the patient.

If the support structure 1 comprises the lateral retention elements 23, the same collaborate with the band means 16 in order to provide an even more stable connection of the at least one frame 2 to the body of the patient.

With the support structure 1 firmly connected to a pre-established portion of the body of a patient, it is possible to proceed with the acquisition of the images necessary for the subsequent surgery operation steps, by means of for example a procedure of computerized tomography, or magnetic resonance or radiography.

Then, based on the acquired data, the various steps of the surgery operation can be planned, including the point of entrance of the surgical tool, the point of arrival, or objective point, and the path that the surgical tool must carry out within the body of the patient.

If the surgery operation is to be executed shortly after the above-indicated acquisition of the images, the support structure 1 is maintained connected to the body of the patient.

If, however, the operation is scheduled several hours or days after the image acquisition procedure, then the support structure 1 is removed from the body of the patient, limiting his discomfort.

In order to proceed with the removal of the support structure from the body of a patient, the band means 16 are released and then the at least one frame 2 is moved away from the body.

During this step, the at least one frame 2 is moved away from the connecting means 8 which are glued/stuck or retained on the body of the patient, up to disengaging the pin elements 14 from the relative seats 15.

With the pin elements 14 disengaged from the relative seats 15, the at least one frame 2 is disconnected from the body of the patient.

Figure 3:
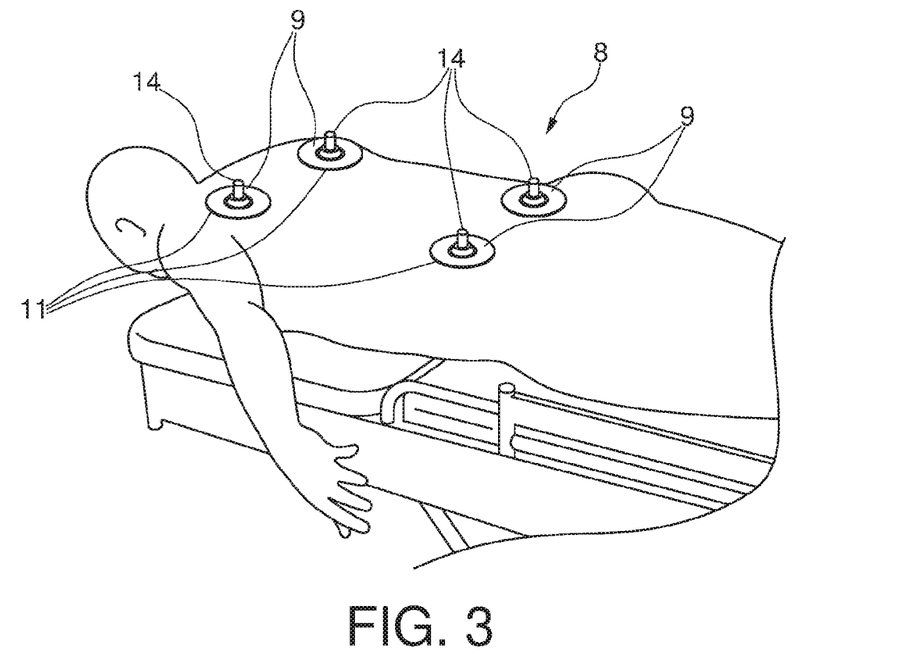
FIG. 3 is a perspective view of several components of the support structure according to the present invention.

The pin elements 14 are instead anchored to the body of the patient in pre-established positions, by means of the respective lower connecting portions 10 (see FIG. 3).

When it is necessary to execute an operation by means of a surgical device 28, one proceeds by repositioning the support structure 1 on the body of the patient in the same position of installation that was previously defined.

In order to reposition the at least one frame 2 on the body of the patient, it is sufficient to orient the lower portion of the frame 7 facing the body of the patient, then align the at least one frame 2 relative to the pin elements 14 glued to the body of the patient so as to place the seats 15 in proximity to the respective pin elements 14.

Then, the at least one frame 2 is moved close to the body of the patient, engaging the single pin elements 14 within the respective seats 15, actually connecting the at least one frame 2 to the body of the patient.

Then, the band means 16 are used for firmly connecting the support structure 1 to the predefined portion of the body of the patient on which it is necessary to operate.

With the support structure 1 firmly connected to the body of the patient, one then proceeds by connecting the surgical device 28 to the upper portion 6 of the at least one frame 2, mutually constraining them.

The surgical device 28, bearing at least one surgical tool 29, can then be commanded by a surgeon or by means of a computerized processor in order to move the tool 29 itself along the previously planned path.

With reference to the above-reported description, it is clear that the support structure 1 for a surgical device according to the present invention is capable of attaining the preset objects.

The support structure 1, indeed, provides a stable support for a surgical device in proximity to a predefined area of a portion of the body of a patient through which a surgery operation is to be executed.

The presence of connecting means 8 and of band means 16 allows firmly connecting the at least one frame 2 to the body of a patient in the scope of a solution that is practical to use and adaptable to the specific morphology of the individual patient. Overall, the support structure 1 has an extremely limited number of components and, moreover, it can be easily moved, thus facilitating its positioning relative to the body of a patient.

The presence of the connecting means 8 allows, if necessary, removing and repositioning the at least one frame 2 in the same predefined position relative to the body of the patient without requiring any percutaneous intervention for such purpose, in the scope of a solution capable of reducing discomfort for the patient himself.

The above-described support structure 1 for a surgical device is susceptible of numerous modifications and variations within the protective scope of the following claims.

The invention claimed is:

1. A support structure configured to be placed on a portion of the human body and usable for supporting a surgical device, said support structure comprising at least one frame delimiting at least one opening defining an area of surgery, wherein said at least one frame has an upper support portion, and a lower portion, said support structure comprising connecting means of said at least one frame to said predefined portion of the human body, wherein said connecting means comprise at least one support operably connectable, in use, in a removable manner, to said at least one frame and to said predefined portion of the human body, without requiring any percutaneous intervention, said at least one support being configured to allow the removal of said at least one frame from said predefined portion of the human body and to provide a reference for the exact repositioning of said at least one frame along said predefined portion of the human body, and comprising a further frame associated with said at least one frame, said further frame providing a support to which at least one surgical device can be associated, wherein said further frame comprises at least one through opening defining the area of surgery and facing the at least one opening of the at least one frame.

2. The support structure according to claim 1, wherein said at least one support comprises a lower connecting portion which can be removably anchored to a predefined portion of the human body.

3. The support structure according to claim 2, wherein said lower connecting portion comprises an adhesive layer or said lower connecting portion comprises suction means, said lower connecting portion being configured to anchor said element to at least one support, in a temporary manner, to said predefined portion of the human body.

4. The support structure according to claim 1, wherein said at least one support comprises an upper connecting portion comprising a pin element engageable, removably in said at least one frame.

5. The support structure according to claim 1, wherein said at least one frame comprises at least one seat engageable by said connecting means.

6. The support structure according to claim 1, wherein said at least one frame is made of radiolucent material.

7. The support structure according to claim 1, comprising lateral retention elements associated with opposite sides of said at least one frame, wherein said lateral retention elements comprise plates configured to be movable to adapt to the dimensions of the predefined portion of the body to be held between them.

8. The support structure according to claim 7, wherein said plates comprise at least one through opening for the operative connection of said band means and said lateral retention elements.

9. A system for positioning and moving a surgical instrument relative to a portion of the human body comprising:
the support structure according to claim 1, at least one surgical device, for the handling and movement of at least one surgical instrument or tool, wherein said at least one surgical device is operatively connectable to said upper portion of said frame or above said additional frame of said support structure.

10. The system for positioning and moving a surgical instrument according to claim 9, wherein said surgical device comprises a Cartesian robot susceptible to retain and translate said at least one surgical instrument along a set of axes orthogonal to each other and to incline said surgical instrument with respect to any one of said orthogonal axes.

11. A method for positioning a support structure for a surgical device relative to a portion of the human body comprising the steps of:
providing one support structure
configured to be placed on a portion of the human body and usable for supporting a surgical device, said support structure comprising at least one frame delimiting at least one opening defining an area of surgery, wherein said at least one frame has
an upper support portion, and a lower portion, said support structure comprising connecting means of said at least one frame to said predefined portion of the human body, wherein said connecting means comprise at least one support operably connectable, in use, in a removable manner, to said at least one frame and to said predefined portion of the human body, without requiring any percutaneous intervention, said at least one support being configured to allow the removal of said at least one frame from said predefined portion of the human body and to provide a reference for the exact repositioning of said at least one frame along said predefined portion of the human body, and comprising a further frame associated with said at least one frame, said further frame providing a support to which at least one surgical device can be associated, wherein said further frame comprises at least one through opening defining the area of surgery and facing the at least one opening of the at least one frame;

positioning said lower portion of said at least one frame in proximity or in contact with a predefined portion of the human body; and associating said support structure with said portion of the human body through said connecting means.

12. The method for positioning said support structure to a predetermined portion of the human body according to claim 11, wherein said positioning said lower portion of said at least one frame comprises placing said connection means in contact with said predetermined portion of the human body and, therefore, connecting said connecting means to said predetermined portion of the human body.

13. A method for repositioning a support structure on a pre-established portion of the human body comprising the steps of:
providing the support structure according to claim 1, with said connecting means operatively connected to said at least one frame;
identifying and defining connection points of said at least one frame along a predetermined portion of the human body;
positioning said at least one frame in contact with a portion of the predetermined human body, carrying said connecting means in contact with said predetermined portion of the human body, constraining supports included in said connecting means to said portion of the human body at said predetermined connection points;
removing said at least one frame from said predetermined portion of the human body until said supports are disengaged from respective seats present along said lower portion of said at least one frame;
separating said at least one frame from said predetermined portion of the human body;
repositioning said at least one frame relating to said predetermined portion of the human body by engaging said supports within said seats.

14. A support structure configured to be placed on a portion of the human body and usable for supporting a surgical device, said support structure comprising at least one frame delimiting at least one opening defining an area of surgery, wherein said at least one frame comprises:
an upper support portion, and a lower portion, said support structure comprising connecting means of said at least one frame to said predefined portion of the human body, wherein said connecting means comprise at least one support operably connectable, in use, in a removable manner, to said at least one frame and to said predefined portion of the human body, without requiring any percutaneous intervention, said at least one support being configured to allow the removal of said at least one frame from said predefined portion of the human body and to provide a reference for the exact repositioning of said at least one frame along said predefined portion of the human body, and further comprising lateral retention elements associated with opposite sides of said at least one frame, wherein said lateral retention elements comprise plates configured to be movable to adapt to the dimensions of the predefined portion of the body to be held between them.

15. The support structure according to claim 14, wherein said plates comprise at least one through opening for the operative connection of said band means and said lateral retention elements.

\* \* \* \* \*